United States Patent [19]

Unemi et al.

[11] 4,371,535
[45] Feb. 1, 1983

[54] METHOD OF AND COMPOSITION FOR DELIVERING 5-FLUOROURACIL TO TUMORS

[75] Inventors: Norio Unemi; Kenji Kitazato; Setsuro Fujii, all of Tokushima, Japan

[73] Assignee: Taiho Pharmaceutical Company Limited, Tokyo, Japan

[21] Appl. No.: 91,530

[22] Filed: Nov. 5, 1979

Related U.S. Application Data

[63] Continuation-in-part of Ser. No. 902,505, May 3, 1978, abandoned, which is a continuation of Ser. No. 735,019, Oct. 22, 1976, abandoned.

[30] Foreign Application Priority Data

Jan. 7, 1976 [GB] United Kingdom ............... 0040776

[51] Int. Cl.$^3$ ............................................. A61K 31/505
[52] U.S. Cl. ................................................... 424/251
[58] Field of Search ........................................ 424/251

[56] References Cited

FOREIGN PATENT DOCUMENTS 50-384  5/1975  Japan ................................ 424/251
1168391 10/1969 United Kingdom .

OTHER PUBLICATIONS

Hedelberger et al., Nature, vol. 179, Mar. 30, 1957, pp. 663–666.
Heidelberger et al., Cancer Research, vol. 18, Apr. 1958, pp. 307–315.
Chemical Abstracts 84:17405t (1976).

Primary Examiner—Jerome D. Goldberg
Attorney, Agent, or Firm—Murray and Whisenhunt

[57] ABSTRACT

A composition containing a pharmacologically effective amount of 1,3-bis(2-tetrahydrofuryl)-5-fluorouracil and an excipient for delivering 5-fluorouracil to cancer cellular tissue of a cancer sensitive to 5-fluorouracil therapy.

12 Claims, No Drawings

METHOD OF AND COMPOSITION FOR DELIVERING 5-FLUOROURACIL TO TUMORS

CROSS-REFERENCE TO RELATED APPLICATIONS

This application is a continuation-in-part of co-pending application Ser. No. 902,505, filed May 3, 1978 now abandoned, which is a continuation of application Ser. No. 735,019, filed Oct. 22, 1976 now abandoned.

This invention relates to an composition, more particularly to an composition containing a 5-fluorouracil derivative as an effective component.

Ever since 5-fluorouracil was found by Heidelberger et al. to inhibit transplanted tumors (Cancer Research, Vol. 18, page 305, 1958 and Nature, Vol, 179, page 663, 1957), the compound has long been used as an anti-tumor agent However, since 5-fluorouracil is highly toxic, it is sometimes impossible to administer the compound over a prolonged period of time and therefore to achieve the desired curing effect. This is attributable to the following reason. The composition is intended to selectively inhibit tumor tissues of tumors sensitive to 5-fluorouracil therapy developing in the living body at an abnormally high rate of proliferation, but 5-fluorouracil, when given, also inhibits relatively rapidly proliferating tissues among normal tissues in the living body such for example as those of the marrow, digestive tract and the like, leading to reduced immunity, gastro-intestinal ulceration, leucopenia and various other side effects. Thus the compound is not usable for long-term administration and fails to achieve an effective cure. In order to overcome the above-mentioned drawback, research has been conducted on 5-fluorouracil derivatives involving low toxicity and less side effects. In 1968 Giller et al. developed 1-(2-tetrahydrofuryl)-5-fluorouracil which is effective as an anti-tumor component for tumors sensitive to 5-fluorouracil therapy in composition and lower in toxicity and less inhibitory on immunity than 5-fluorouracil (British Pat. No. 1,168,391) by delivering 5-fluorouracil to cancer cellular tissue of a cancer sensitive to 5-fluorouracil therapy. However, it is desired to further improve the activity, toxicity and side effects of the composition.

An object of this invention is to provide an composition for delivering 5-fluorouracil to cancer cellular tissue of a cancer sensitive to 5-fluorouracil therapy having a more excellent action than the above-mentioned known compositions.

Another object of this invention is to provide an composition for delivering 5-fluorouracil to cancer cellular tissue of a cancer sensitive to 5-fluorouracil therapy having lower toxicity and lower immunity inhibiting action than those heretofore known.

Another object of this invention is to provide an composition for delivering 5-fluorouracil to cancer cellular tissue of a cancer sensitive to 5-fluorouracil therapy which has less side effects and which can be administered continually for a prolonged period of time.

The above and other objects and features of this invention will become more apparent from the following description.

The composition of this invention contains a pharmacologically effective amount of 1,3-bis(2-tetrahydrofuryl)-5-fluorouracil and an excipient.

Our researches have revealed that 1,3-bis(2-tetrahydrofuryl)-5-fluorouracil has more excellent anti-tumor activity, lower toxicity and less side effects than 1-(2-tetrahydrofuryl)-5-fluorouracil.

The compound 1,3-bis(2-tetrahydrofuryl)-5-fluorouracil to be used in this invention is already known and is represented by the formula

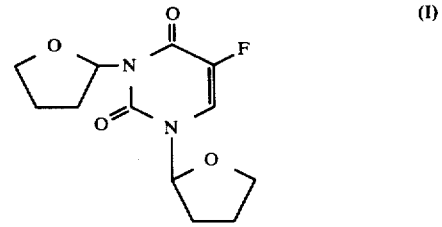

The compound is in the form of white crystals and is soluble in methanol, ethanol, acetone, ether, chloroform, glacial acetic acid, dimethyl sulfoxide, etc. and sparingly soluble in water, aqueous caustic soda solution, ethyl acetate, hydrochloric acid, etc.

The effective component of the anti-tumor composition of this invention, i.e. 1,3-bis(2-tetrahydrofuryl)-5-fluorouracil, is prepared, for example, by reacting 2,4-bis(trimethylsilyl)-5-fluorouracil with 2-acyloxytetrahydrofuran in the presence of Lewis acid. The reaction is represented by the following equation.

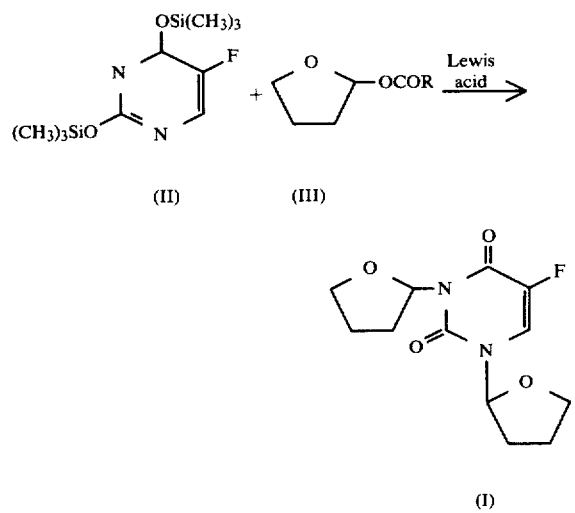

wherein R is lower alkyl or phenyl.

The 2,4-bis(trimethylsilyl)-5-fluorouracil (II) is a known compound and is prepared, for example, by reacting 5-fluorouracil with excess hexamethyldisilazane at elevated temperatures and distilling the reaction mixture in nitrogen atmosphere to remove the unreacted hexamethyldisilazane. The resulting oily substance is usable as the starting material (II) as it is or may be distilled to isolate 2,4-bis(trimethylsilyl)-5-fluorouracil (II). The other starting material, i.e. 2-acyloxytetrahydrofuran (III), is also a known compound and easily available in the art.

Generally, the reaction between 2,4-bis(trimethylsilyl)-5-fluorouracil (II) and 2-acyloxytetrahydrofuran (III) is carried out preferably with use of an excess amount of the latter relative to the former. More specifically, it is preferable to use about 2.2 to 4 moles of the latter per mole of the former. The Lewis acid to be used for the reaction may be any of those heretofore known such as stannic chloride, titanium tetrachloride, silicon tetrachloride, antimony pentachloride, boron trifluoride-ethyl ether complex compound, etc., among which stannic chloride is especially preferable. The amount of the Lewis acid to be used is variable over a considerably wide range. Advantageously, about 0.001 to 0.5 mole of the acid is used per mole of 2,4-bis(trimethylsilyl)-5-fluorouracil. It is not desirable to use a large quantity of Lewis acid, since the acid will then promote decomposition of the desired product. The reaction is conducted in a nonprotonic solvent such as acetonitrile, nitromethane, dichloromethane, dichloroethane, toluene or the like, among which dichloromethane and dichloroethane are advantageous. The reaction is conducted at −50° C. to room temperature. When a relatively large amount of Lewis acid is used, it is advantageous to effect the reaction at a lower temperature to prevent decomposition of the desired product. Usually the reaction takes about 0.5 to 10 hours. The progress of the reaction is ascertainable by thin-layer chromatography for example by using silica gel as an adsorbing agent and a chloroform-ethanol mixture (5:1) as a developer. Since the reaction gives a small amount of 1-(2-tetrahydrofuryl)-5-fluorouracil as a by-product, the desired product is, for example, isolated and purified in the following manner. The mixture resulting from the reaction is neutralized with an aqueous solution or alcohol solution of alkali metal hydroxide, carbonate or bicarbonate or of ammonia, and the precipitate is filtered off. The organic layer obtained by separating the aqueous layer is concentrated at a reduced pressure, the residue is dissolved in chloroform or the like, an alkali aqueous solution is added to the solution, and the mixture is shaken to transfer 1-(2-tetrahydrofuryl)-5-fluorouracil to the aqueous layer. After removing the aqueous layer, the chloroform layer is washed with water and then concentrated to obtain crude crystals. Recrystallization from alcohol or n-hexane gives the desired 1,3-bis(2-tetrahydrofuryl)-5-fluorouracil in a high yield.

The composition of this invention contains a pharmacologically effective amount of 1,3-bis(2-tetrahydrofuryl)-5-fluorouracil and an excipient.

The anti-tumor composition of this invention can be formulated as various pharmaceutical preparations for varying routes of administration. For oral administration, capsules, tablets, granules, syrups are available. Non-oral preparations include injectable solutions, suppositories, etc. For local administration, ointments are available. In view of the ease of formulation and storage stability, the composition may preferably be used in the form of capsules, suppositories and ointments.

The excipients useful for making oral preparations such as capsules, tablets, granules, syrups, etc. are for example lactose, sucrose, starch, talc, magnesium stearate, crystalline cellulose, methyl cellulose, carboxymethyl cellulose, glycerin, sodium alginate, gum arabic, etc. The amount of the effective component in oral preparations may preferably be 200 to 400 mg per dosage unit. Suitable carriers for preparing suppositories are for example cacao butter, Witepsol-W35 (fat, trade mark of Dynamit Nobel A.G. of Germany). The suppositories may preferably contain 500 to 1,000 mg of the effective component per piece. The dose per day of such oral preparations, suppositories, etc. for systemic administration may suitably be 800 to 1,200 mg calculated as the effective component.

Examples of suitable carriers for ointments for local administration are liquid paraffin, cetyl alcohol, white vaseline, squalane, hydrous lanolin, cholesterol and like oily or fatty materials. Preferably the amount of effective component of ointments is 5 to 10 wt.%.

Given below are an example for illustrating the preparation of 1,3-bis(2-tetrahydrofuryl)-5-fluorouracil, examples of anti-tumor compositions of this invention and the results of biological activity tests of the drug.

Preparation of 1,3-bis(2-tetrahydrofuryl)-5-fluorouracil.

A 26.0 quantity of 5-fluorouracil and 38.7 g of hexamethyldisilazane are stirred at 150° to 160° C. for 4 hours. The reaction mixture is distilled in a nitrogen atmosphere at a temperature of not higher than 100° C. at a reduced pressure of 20 mm Hg to remove the excess hexamethyldisilazane. The oily residue is dissolved in 250 ml of absolute dichloromethane, 0.5 g of anhydrous stannic chloride is added to the solution, and 59 g of 2-acetoxy-tetrahydrofuran is then added dropwise to the mixture at −20° C. The resulting mixture is stirred at room temperature for 5 hours. After the reaction, the mixture is neutralized with a mixture of ammonia water (30 wt.%) and methanol (in a volume ratio of 1:1), and the precipitate is filtered off. The organic layer of the filtrate is concentrated at a reduced pressure, the residue is dissolved in 500 ml of chloroform, a 10 wt.% aqueous solution of sodium carbonate is added to the solution, and the mixture is shaken. After removing the aqueous layer, the chloroform layer is washed with water and concentrated to obtain crude crystals. Recrystallization from ethanol gives 48.7 g of 1,3-bis(2-tetrahydrofuryl)-5-fluorouracil in the form of white crystals, m.p. 105° to 108° C. (Yield: 90.1 mole %).

| Elementary analysis (for $C_{12}H_{15}N_2O_4F$) | | | |
|---|---|---|---|
| | H | C | N |
| Calcd. (%): | 5.94 | 53.33 | 10.37 |
| Found (%): | 5.77 | 53.18 | 10.37 |

EXAMPLE 1

A 6 g quantity of magnesium stearate and 44 g of lactose are thoroughly stirred to prepare a uniform mixture, to which 50 g of lactose and 100 g of crystalline cellulose are further added, and the mass is stirred. Finely divided 1,3-bis(2-tetrahydrofuryl)-5-fluorouracil (200 g) is then admixed with the resulting mixture to obtain a powdery preparation. The preparation is encapsulated to produce capsules each containing 400 mg of the powdery preparation.

EXAMPLE 2

A 3 g quantity of magnesium stearate, 10 g of carboxymethyl cellulose calcium and 50 of crystalline cellulose are stirred to obtain a uniform mixture, to which 200 g of finely divided 1,3-bis(2-tetrahydrofuryl)-5-fluorouracil is then admixed. The mixture is made into slugs by a slugging machine, then granulated by an oscillator equipped with a No. 10 screen, and the granules are separated by a No. 30 screen, the screens being those specified by the Japanese Pharmacopoeia. A 3 g quantity of magnesium stearate is added to the granules remaining on the screen, and the mixture is made into crude tablets, each of the tablets weighing 266 mg. The tablets can be sugar- or film-coated.

EXAMPLE 3

A 1,400 g quantity of Witepsol-W35 (trade mark, as defined before) is melted by heating to 60° C., and 750 g of finely divided 1,3-bis(2-tetrahydrofuryl)-5-fluorouracil is added in small portions to the molten mass to obtain a uniform mixture by stirring. The mixture is then cooled to 40° C. and thereafter placed into ten plastic containers each in a specified amount. The containers are passed through a cooling tank at 15° to 20° C. to solidify the contents. The opening of each container is sealed to prepare suppositories.

EXAMPLE 4

A 100 g quantity of liquid paraffin, 50 g of cetyl alcohol and 797 g of vaseline are melted at an elevated temperature of 80° C., and 3 g of cholesterol and 50 g of finely divided 1,3-bis(2-tetrahydrofuryl)-5-fluorouracil are then added to the molten mixture with thorough stirring. The resulting mixture is allowed to stand at room temperature and, when solidified to suitable hardness, the mixture is filled into a container to prepare an ointment.

Biological activity tests of the anti-tumor composition of this invention

1. Acute toxicity test of 1,3-bis(2-tetrahydrofuryl)-5-fluorouracil

Mice (ddy strain, male, 5 weeks old) are reared for one week, then fasted for 15 hours and thereafter orally given the compound forcibly. After the administration, the mice are placed into plastic cages, with free access to a solid diet and water, and checked for mortality 3 days, one week, 2 weeks and 3 weeks later. $LD_{50}$ is calculated according to the method of Litchfield and Wilcoxon. The results are given in Table 1. As a control drug, 1-(2-tetrahydrofuryl)-5-fluorouracil is used.

TABLE 1

| | Compound | |
|---|---|---|
| Period | 1,3-bis(2-Tetrahydro-furyl)-5-fluorouracil | 1-(2-Tetrahydrofuryl)-5-fluorouracil |
| 3 days | 2,985 mg/kg | 1,000 mg/kg |
| 1 week | 2,780 mg/kg | 960 mg/kg |
| 2 weeks | 2,664 mg/kg | 900 mg/kg |
| 3 weeks | 2,564 mg/kg | 800 mg/kg |

2. Anti-tumor activity of 1,3-bis(2-tetrahydrofuryl)-5-fluorouracil

As transplantable tumors, Ehrlich carcinoma and sarcoma 180 are used for mice and Yoshida sarcoma and AH 130 for rats. Cells of the tumor, $5 \times 10^6$ in number, are subcutaneously transplanted in the inguinal region of test animals (10 in each group). Twenty-four hours after the transplantation, 121.5 mg/kg of 1,3-bis(2-tetrahydrofuryl)-5-fluorouracil or 90 mg/kg (equimolar relative to the former) of 1-(2-tetrahydrofuryl)-5-fluorouracil is orally administered, as suspended in 5 wt.% aqueous solution of gum arabic, to the animals once daily for 7 consecutive days. The effect of the compound is determined in terms of the weight of tumor on the 10th day from the transplantation. The results are given in Tables 2 to 5.

TABLE 2

| (Anti-tumor activity on Ehrlich carcinoma) | | |
|---|---|---|
| Compound | Weight of tumor (g) | Inhibition percentage |
| 1,3-bis(2-Tetrahydrofuryl)-5-fluorouracil | 0.26 ± 0.06 | 57 |
| 1-(2-Tetrahydrofuryl)-5-fluorouracil (control drug) | 0.37 ± 0.14 | 39 |
| Control (none) | 0.61 ± 0.08 | — |

TABLE 3

| (Anti-tumor activity on sarcoma 180) | | |
|---|---|---|
| Compound | Weight of tumor (g) | Inhibition percentage |
| 1,3-bis(2-Tetrahydrofuryl)-5-fluorouracil | 0.31 ± 0.10 | 69 |
| 1-(2-Tetrahydrofuryl)-5-fluorouracil (control drug) | 0.36 ± 0.11 | 64 |
| Control (none) | 1.00 ± 0.09 | — |

TABLE 4

| (Anti-tumor activity on Yoshida sarcoma) | | |
|---|---|---|
| Compound | Weight of tumor (g) | Inhibition percentage |
| 1,3-bis(2-Tetrahydrofuryl)-5-fluorouracil | 2.59 ± 0.33 | 42 |
| 1-(2-Tetrahydrofuryl)-5-fluorouracil (control drug) | 3.48 ± 0.68 | 22 |
| Control (none) | 4.48 ± 0.60 | — |

TABLE 5

| (Anti-tumor activity on AH-130) | | |
|---|---|---|
| Compound | Weight of tumor (g) | Inhibition percentage |
| 1,3-bis(2-Tetrahydrofuryl)-5-fluorouracil | 0.92 ± 0.35 | 56 |
| 1-(2-Tetrahydrofuryl)-5-fluorouracil (control drug) | 1.11 ± 0.17 | 47 |
| Control (none) | 2.10 ± 0.50 | — |

3. Inhibitory action of 1,3-bis(2-tetrahydrofuryl)-5-fluorouracil on the cellular immunity as determined by delayed cutireaction A predetermined amount of 7 wt. % ethanol solution of picryl chloride is given to the shaved abdomens of mice for sensitization. For 6 days from the first day after the sensitization, 121.5 mg/kg of 1,3-bis(2-tetrahydrofuryl)-5-fluorouracil or 90 mg/kg (equimolar relative to the former) of 1-(2-tetrahydrofuryl)-5-fluorouracil is orally administered, as suspended in 5 wt. % aqueous solution of gum arabic, to the animals daily. On the seventh day after the sensitization, a 1 wt. % olive oil solution of picryl chloride is applied to the inside of both ears of each animal to give rise to a delayed cutireaction. The thickness of the ear resulting from the reaction in 24 hours is measured to calculate the percentage of inhibition on immunity. The results are listed in Table 6.

TABLE 6

| Compound | Thickness of ear ($\times 10^{-3}$ cm) | Inhibition percentage |
|---|---|---|
| 1,3-bis(2-Tetrahydrofuryl)-5-fluorouracil | 21.9 ± 2.2 | 19 |

TABLE 6-continued

| Compound | Thickness of ear ($\times 10^{-3}$ cm) | Inhibition percentage |
|---|---|---|
| 1-(2-Tetrahydrofuryl)-5-fluorouracil (control drug) | 19.9 ± 4.2 | 27 |
| Control (none) | 27.2 ± 4.4 | — |

4. Variations of the concentration of 5-fluorouracil in the blood and in the cancer cellular tissue with the lapse of time when 1,3-bis(2-tetrahydrofuryl)-5-fluorouracil is administered to rats having cancer:

Cells of the tumor, AH-130, $5 \times 10^6$ in number, are subcutaneously transplanted in the armpit region of test animals (3 in each group). One week after the transplantation, each 1 m mole/kg of 1,3-bis(2-tetrahydrofuryl)-5-fluorouracil and 1-(2-tetrahydrofuryl)-5-fluorouracil are orally administered, as suspended in water, to the animals. The concentration of 5-fluorouracil in the blood and in the cancer cellular tissue of the animals are measured 1, 2, 4, 8 and 12 hours after the administration. The results are shown in Tables 7 and 8.

TABLE 7

(Variations of the concentration of 5-fluorouracil in blood)

| Compound | Lapse of time | | | | |
|---|---|---|---|---|---|
|  | 1 hr | 2 hr | 4 hr | 8 hr | 12 hr |
| 1,3-bis(2-Tetrahydrofuryl)-5-fluorouracil | 5.88 | 5.08 | 2.65 | 0.57 | 0.20 |
| 1-(2-Tetrahydrofuryl)-5-fluorouracil | 0.20 | 0.30 | 0.20 | 0.08 | up to 0.04 |

(unit: μg/ml)

TABLE 8

(Variations of the concentration of 5-fluorouracil in cancer cellular tissue)

| Compound | Lapse of time | | | | |
|---|---|---|---|---|---|
|  | 1 hr | 2 hr | 4 hr | 8 hr | 12 hr |
| 1,3-bis(2-Tetrahydrofuryl)-5-fluorouracil | 8.93 | 7.53 | 7.53 | 5.40 | 2.13 |
| 1-(2-Tetrahydrofuryl)-5-fluorouracil | up to 0.20 | 0.35 | 0.35 | 0.34 | up to 0.20 |

(unit: μg/ml)

The results of biological activity tests of the present composition reveal the following advantages over the known composition containing 1-(2-tetrahydrofuryl)-5-fluorouracil as an effective component. The present composition has an excellent anti-tumor activity by delivering 5-fluorouracil to cancer cellular tissue of a cancer sensitive to 5-fluorouracil therapy, which is 1 to 2 times the effect of the conventional composition, although the effect varies with the type of the tumor used for testing. It has a lower inhibitory effect on the cellular immunity and only about one-third the acute toxicity of the conventional composition. Further the concentration of 5-fluorouracil maintained by the present composition in the blood and cancer cellular tissue of test animals for a prolonged period of time is about 10 to 20 times as high as that afforded by the conventional composition. Thus the present composition is much superior to the composition heretofore used.

As will be appreciated from the 5-fluorouracil concentration values reported hereinabove, the composition of the present invention functions in the manner of a prodrug. That is, the 1,3-bis(2-tetrahydrofuryl)-5-fluorouracil in the composition of the present invention is converted in the body into 5-fluorouracil. The concentration of 5-fluorouracil maintained in the cancer cellular tissue of test animals for a prolonged period of time is much higher when the 5-fluorouracil is derived from the compound 1,3-bis(2-tetrahydrofuryl)-5-fluorouracil than when the 5-fluorouracil is derived from the compound 1-(2-tetrahydrofuryl)-5-fluorouracil. The composition of the present invention thus functions as a delivery system for delivering 5-fluorouracil to a tumor in a patient. The tumors which respond to the present treatment are those tumors which are sensitive to 5-fluorouracil therapy. Thus, as will be clear from the values reported in Table 8 hereinabove, cancers sensitive to 5-fluorouracil therapy are treated by administering to a patient having such cancer an effective amount of the compound 1,3-bis(2-tetrahydrofuryl)-5-fluorouracil, together with a pharmaceutical excipient. The excipient is, preferably, sterile.

As known to those in the art, the cancers which are sensitive to 5-fluorouracil therapy include breast cancer, cancer of the esophagus, lung cancer, liver cancer and cancers of the gastro-intestinal system, such as stomach cancer, cancers of the intestines, cancer of the rectum, and the like.

What is claimed is:

1. A method of delivering 5-fluorouracil to a cancer in a patient, wherein the cancer is sensitive to 5-fluorouracil therapy, said method comprising administering to said patient an amount of 1,3-bis(2-tetrahydrofuryl)-5-fluorouracil which is effective to deliver an anti-cancer effective amount of 5-fluorouracil to said cancer.

2. Method of claim 1, wherein said 1,3-bis(2-tetrahydrofuryl)-5-fluorouracil is administered to said patient in the amount of up to about 1200 mg per day.

3. Method of claim 2, wherein said 1,3-bis(2-tetrahydrofuryl)-5-fluorouracil is administered orally.

4. Method of claim 2, wherein said 1,3-bis(2-tetrahydrofuryl)-5-fluorouracil is locally administered to a patient in the form of an ointment.

5. Method of claim 1, wherein the 1,3-bis(2-tetrahydrofuryl)-5-fluorouracil is administered to said patient in a systemic manner.

6. Method of claim 5, wherein the 1,3-bis(2-tetrahydrofuryl)-5-fluorouracil is systemically administered to said patient at a dosage level of up to about 100 mg per day.

7. Composition for delivering 5-fluorouracil to cancer cellular tissue of a cancer sensitive to 5-fluorouracil therapy, said composition comprising an excipient and a sterile pharmaceutical 1,3-bis(2-tetrahydrofuryl)-5-fluorouracil in an amount which is effective to deliver an anti-cancer effective amount of 5-fluorouracil to the cancer.

8. A composition in the form of a capsule, tablet, granule or syrup containing 200 to 400 mg of 1,3-bis(2-tetrahydrofuryl)-5-fluorouracil per dosage unit and a pharmaceutical excipient.

9. A composition in the form of a suppository containing 500 to 1000 mg per unit of 1,3-bis(2-tetrahydrofuryl)-5-fluorouracil and a pharmaceutical excipient.

10. A composition for oral administration for delivering 5-fluorouracil to cancer cellular tissue of a cancer sensitive to 5-fluorouracil therapy, said composition comprising an effective amount of 1,3-bis(2-tetrahydrofuryl)-5-fluorouracil and a sterile pharmaceutical excipient, wherein the composition contains 200 to 400 mg. of said 1,3-bis(2-tetrahydrofuryl)-5-fluorouracil per dosage unit.

11. A composition for delivering 5-fluorouracil to cancer cellular tissue of a cancer sensitive to 5-fluorouracil therapy, said composition comprising an effective amount of 1,3-bis(2-tetrahydrofuryl)-5-fluorouracil and an excipient, said composition in the form of a suppository containing 500 to 1000 mg. of 1,3-bis(2-tetrahydrofuryl)-5-fluorouracil.

12. A composition for delivering 5-fluorouracil to cancer cellular tissue of a cancer sensitive to 5-fluorouracil therapy, said composition comprising an effective amount of 1,3-bis(2-tetrahydrofuryl)-5-fluorouracil and an excipient, said composition being in the form of an ointment containing 5 to 10 weight percent of 1,3-bis(2-tetrahydrofuryl)-5-fluorouracil.

* * * * *